US006471688B1

United States Patent
Harper et al.

(10) Patent No.: US 6,471,688 B1
(45) Date of Patent: Oct. 29, 2002

(54) OSMOTIC PUMP DRUG DELIVERY SYSTEMS AND METHODS

(75) Inventors: Derek J. Harper, Santa Barbara, CA (US); Charles F. Milo, Atherton, CA (US)

(73) Assignee: MicroSolutions, Inc., Santa Barbara, CA (US)

( * ) Notice: Subject to any disclaimer, the term of this patent is extended or adjusted under 35 U.S.C. 154(b) by 0 days.

(21) Appl. No.: 09/503,821

(22) Filed: Feb. 15, 2000

(51) Int. Cl.$^7$ ............................................. A61M 31/00
(52) U.S. Cl. ............................ 604/892.1; 604/891.1; 424/424
(58) Field of Search .................... 604/890.1, 891.1, 604/892.1; 424/422, 424

(56) References Cited

U.S. PATENT DOCUMENTS

| | | | |
|---|---|---|---|
| 3,760,984 A | | 9/1973 | Theeuwes |
| 3,845,770 A | | 11/1974 | Theeuwes |
| 3,916,899 A | | 11/1975 | Theeuwes |
| 3,977,404 A | | 8/1976 | Theeuwes |
| 3,987,790 A | | 10/1976 | Eckenhoff |
| 4,455,143 A | * | 6/1984 | Theeuwes et al. ........ 604/892.1 |
| 4,587,117 A | | 5/1986 | Edgren |
| 4,808,152 A | * | 2/1989 | Sibalis ...................... 604/20 |
| 5,205,820 A | * | 4/1993 | Kriesel .................... 604/890.1 |
| 5,607,696 A | | 3/1997 | Rivera |
| 5,693,019 A | * | 12/1997 | Kriesel .................... 604/890.1 |
| 5,728,396 A | | 3/1998 | Peery et al. |
| 5,798,114 A | * | 8/1998 | Elsberry et al. ......... 604/892.1 |
| 5,869,097 A | | 2/1999 | Wong |
| 5,919,160 A | * | 7/1999 | Sanfilippo, II ........... 604/891.1 |

FOREIGN PATENT DOCUMENTS

WO     WO 00/54745     3/1999

OTHER PUBLICATIONS

Jon P. Monk, Rosemary Beresford and Alan Ward, *Sufentanil: A Review Of Its Pharmacological And Therapeutic Use*, Drugs 36, pp. 286–313, 1988.

(List continued on next page.)

Primary Examiner—J. Casimer Jacyna
(74) Attorney, Agent, or Firm—Young Law Firm, P.C.

(57) ABSTRACT

Implantable osmotic pump devices and systems include multiple osmotic pumps and/or semipermeable membranes to extend the useful life cycle and functionality of the drug delivery system. Use of an implantable system including multiple implantable osmotic pumps allows different drugs to be administered from the same implanted system. One or more of the semipermeable membranes of the system may be initially sealed by an overlying impermeable membrane upon implantation of the system into the patient. When the patient develops a tolerance to a first drug or to a first dose of the first drug, the impermeable membrane may be breached, to expose the underlying semipermeable membrane to the osmotic pressure of the patient at the implant site. This causes the infusion rate to increase, thereby providing the patient with the needed relief and/or other desired therapeutic effect. In the case of a multiple pump system, breaching an impermeable membrane may cause the infusion of a second drug. The second drug may potentiate a therapeutic effect (such as an analgesic effect) of the first drug, as is the case with Sufentanil and Clonidine.

39 Claims, 4 Drawing Sheets

OTHER PUBLICATIONS

F.P. Boersma, M.D.; H. Noorduin, M.SC. and G. Vanden Bussche, M.D., *Epidural Sufentanil For Cancer Pain Control In Outpatients*, Regional Anestehesia, Nov.–Dec. vol. 14, No. 6, pp. 293–297, 1989.

Tim J. Lamer, M.D.; Symposium on Pain Management–Part II, *Treatment Of Cancer–Related Pain: When Orally Administered Medications Fail,* Mayo Clinic Proc., 69, pp. 473–480, 1994.

Alzet Osmotic Pumps, *References from 1991–1998 On The Administration Of Opiods Using ALZET Osmotic Pumps (OPIO–Q4–99)*, pp. 1–13, World Wide Web, http://www.alzet.com/bibliography/bib_pages/opio.htm (Printed on Oct. 13, 2000).

Mercier FJ; Dounas M; Bouaziz; Des Mesnards–Smaja V; Foiret C; Vestermann MN; Fischler M; Benhamou D. "The effect of adding a minidose of clonidine to intrathecal sufentanil for labor analgesia." Anesthesiology Sep. 1998;89(3):594–601.

Meert TF; De Kock M; "Potentiation of the analgesic properties of fentanyl–like opioids with alpha 2–adrenoceptor agonists in rats." Anesthesiology Sep. 1994;81(3):677–88.

Paix A; Coleman A; Lees J; Grigson J; Brooksbank M; Thorne D; Ashby M. "Subcutaneous fentanyl and sufentanil infusion substitution for morphine intolerance in cancer pain management." Pain Nov. 1995;63(2):263–9.

* cited by examiner

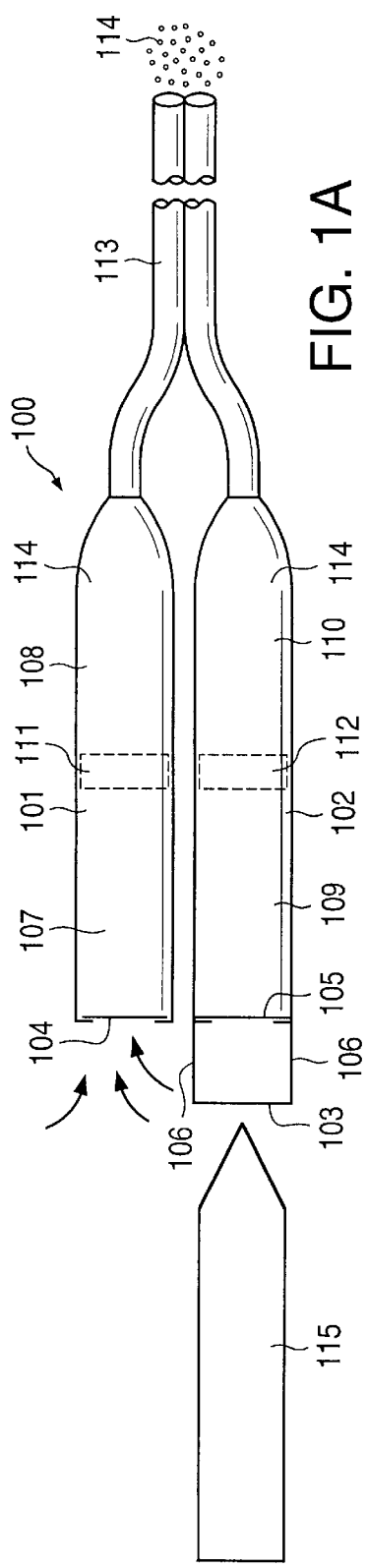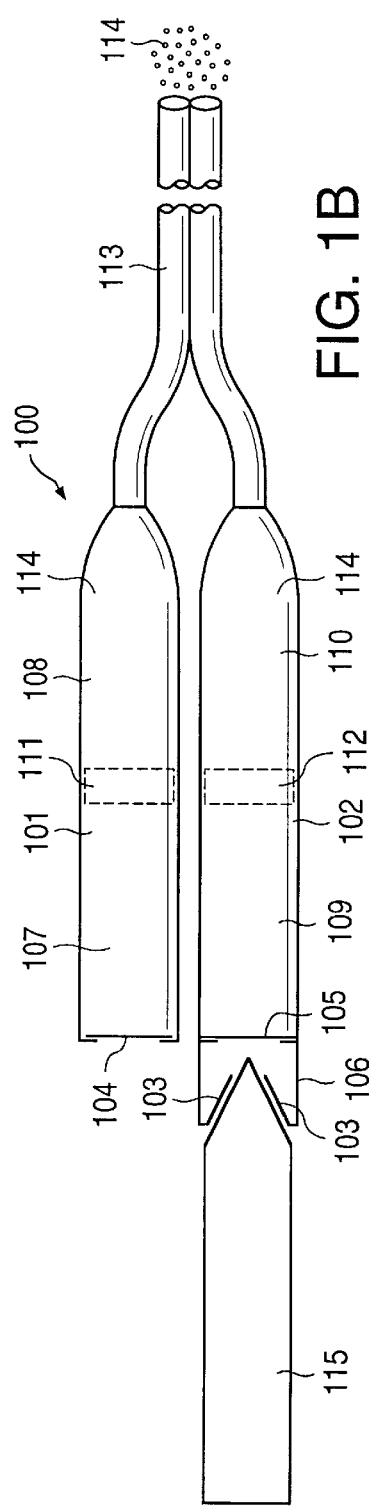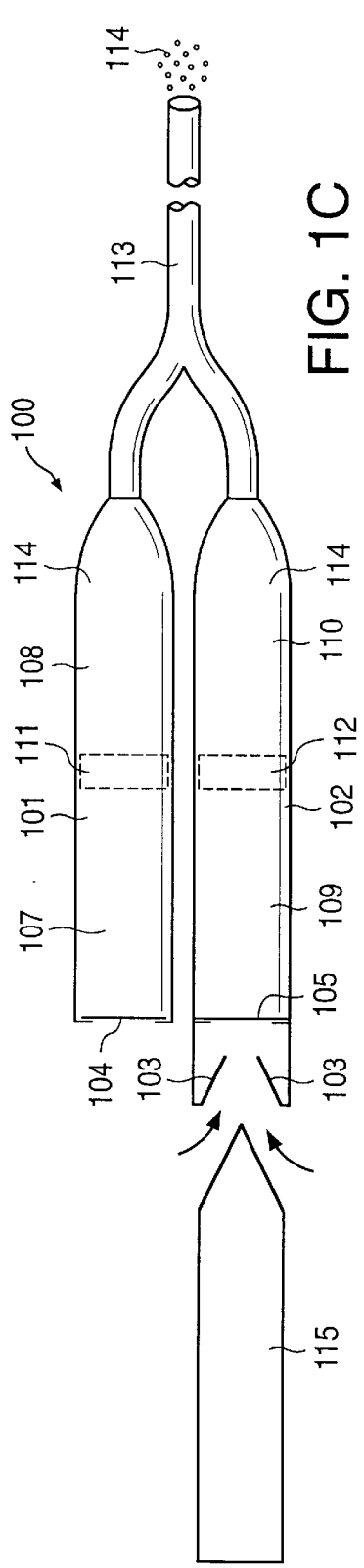

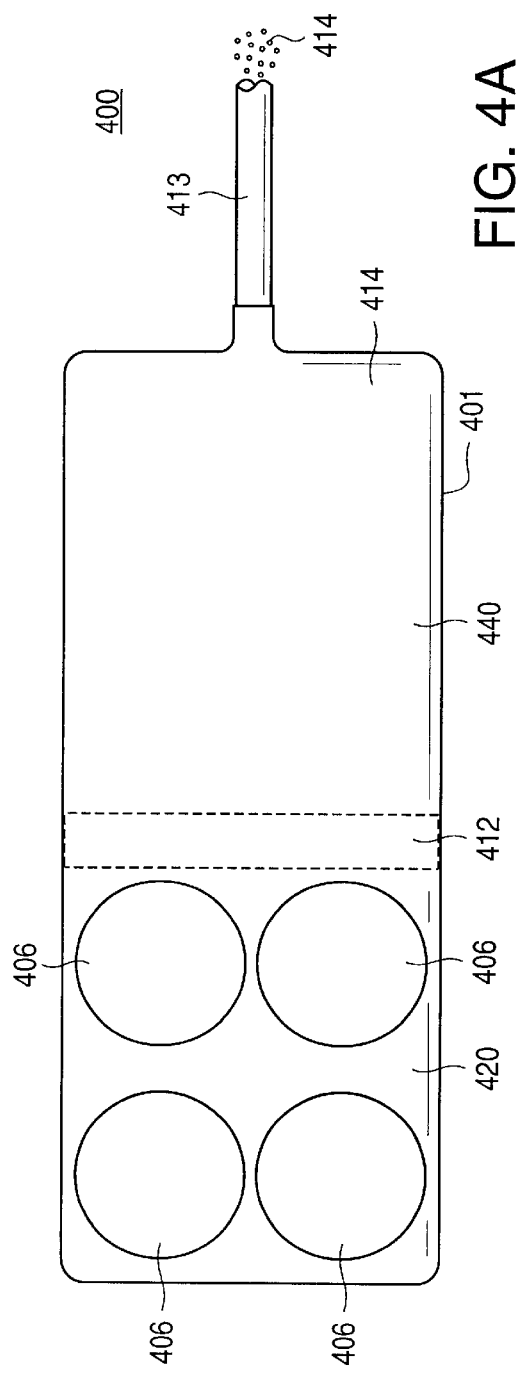
FIG. 4A
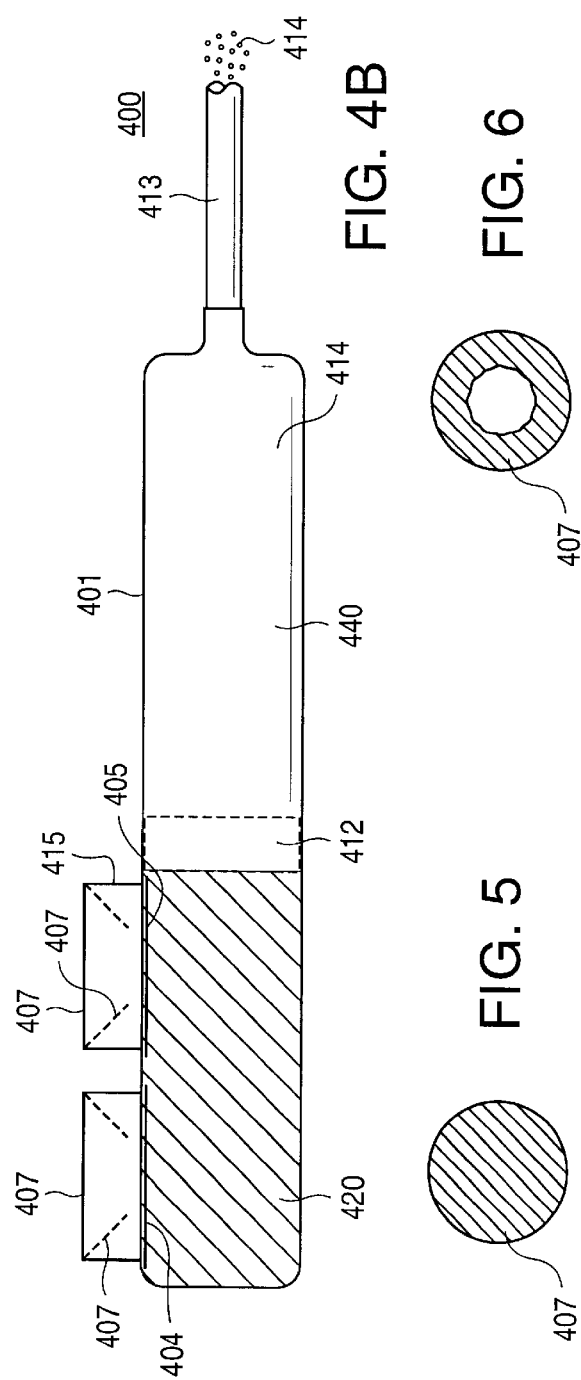
FIG. 4B
FIG. 5
FIG. 6

OSMOTIC PUMP DRUG DELIVERY SYSTEMS AND METHODS

CROSS-REFERENCE TO RELATED APPLICATIONS

This application is related in subject matter to commonly assigned co-pending patent application Ser. No. 09/442,128 filed on Nov. 16, 1999 entitled "Methods And Implantable Devices And Systems For Long Term Delivery Of A Pharmaceutical Agent", the disclosure of which is hereby incorporated herein in its entirety.

This application is also related in subject matter to commonly assigned co-pending patent application Ser. No. 09/504,603 filed on Feb. 15, 2000 and entitled "Osmotic Pup Delivery System With Pre-Hydrated Membranes(s) And/Or Primable Cather", the disclosure of which is also hereby incorporated herein in its entirety.

This application is also related in subject matter to commonly assigned co-pending patent application Ser. No. 09/504,971 filed on Feb. 15, 2000 and entitled "Osmotic Pump Delivery System With Flexible Drug Compartment", the disclosure of which is also hereby incorporated herein in its entirety.

BACKGROUND OF THE INVENTION

1. Field of the Invention

The present invention relates generally to the field of drug delivery systems. In particular, the present invention relates to osmotic pump systems, devices, kits and associated methods for shortening the time interval between implantation of the osmotic pump system and delivery of a pharmaceutical agent to the patient. The present invention also relates to osmotic implantable systems and methods for delivering multiple drugs simultaneously (and/or sequentially), implantable osmotic systems having redundant pumps, as well as systems, methods and kits for delivering mixtures of drugs and/or potentiating drugs.

2. Description of the Related Art

Since the beginning of modern medicine, drugs have been administered orally. Patients have taken pills as recommended by their physician. The pills must pass through the digestive system and then the liver before they reach their intended delivery site (e.g., the vascular system). The actions of the digestive tract and the liver often reduce the efficacy of medication; furthermore, medications delivered systemically sometimes cause undesirable side effects. Over the course of the past few decades, drug delivery technology and administration has evolved from oral delivery to site-specific delivery. In addition to the oral route of administration, drugs are also routinely administered via the vascular system (intravenous or IV). Intravenous drug delivery has the advantage of bypassing the acidic and enzymatic action of the digestive system. Unfortunately, IV administration requires the use of a percutaneous catheter or needle to deliver the drug to the vein. The percutaneous site requires extra cleanliness and maintenance to minimize the risk of infection. Infection is such a significant risk that IV administration is often limited to a number of weeks, at most. In addition, the patient must wear an external pump connected to the percutaneous catheter.

The next step in the evolution of drug delivery was the implanted pump. The implanted pump is a device that is completely implanted under the skin of a patient, thereby negating the need for a percutaneous catheter. These implanted pumps provide the patient with a drug at a constant or a programmed delivery rate. Constant rate or programmable rate pumps are based on either phase-change or peristaltic technology. When a constant, unchanging delivery rate is required, a constant-rate pump is well suited for long-term implanted drug delivery. If changes to the infusion rate are expected, a programmable pump may be used in place of the constant rate pump. Fully implanted constant rate and programmable rate infusion pumps have been sold in the United States for human use since the late 1970s and early 1980s, respectively. Two problems associated with such 1970s and 1980s vintage constant rate and programmable rate infusion pumps relate to their size and their cost. Current implantable constant rate and programmable pumps are about the size and shape of hockey pucks, and they typically are sold to the hospital for $5,000–$9,000. The current implantable pumps must be implanted in the Operating Room under general anesthesia, which further increases costs, as well as the risk, and discomfort to the patient. The size and cost of such pumps has proven to be a substantial barrier to their use, and they are rarely used to deliver medication. An added drawback of phase-change and peristaltic pumps is that they must be refilled with drug every 3–8 weeks. Refills constitute an added burden to the caregiver, and add further costs to an already overburdened healthcare system. The burden associated with such refills, therefore, further limits the use of phase-change and peristaltic pumps.

In the 1970s, a new approach toward implanted pump design was commercialized for animal use only. The driving force of the pumps based upon this new approach utilized the principle of osmosis. Osmotic pumps may be much smaller than other constant rate or programmable pumps, because their infusion rate can be very low. An example of such a pump is described listed in U.S. Pat. No. 5,728,396, the disclosure of which is hereby incorporated herein in its entirety. This patent discloses an implantable osmotic pump that achieves a sustained delivery of leuprolide. The pump includes an impermeable reservoir that is divided into a water-swellable agent chamber and a drug chamber. Fluid from the body is imbibed through a semipermeable plug into the water-swellable agent chamber and the drug is released through a diffusion outlet at a substantially constant rate.

However, osmotic pumps of this type are configured to deliver a single drug (or a single combination of drugs) at a time and at a single delivery rate. Should the patient develop a tolerance to the drug and require an increased dose to alleviate pain, for example, such a single drug/single dose pump is unable to provide the needed relief. In such a case, the physician may need to supplement the drug delivered by the implanted pump with another drug or more of the same drug, delivered via an intravenous route, for example. This, however, defeats the purpose of the implanted pump, namely to provide a self-contained drug delivery system that operates with little or no discomfort to the patient. What are needed, therefore, are novel implantable pumps and pump systems able to deliver a drug at more than a single rate.

There may be instances, moreover, when a simple increased dose of the same drug is ineffective to achieve the desired therapeutic result. In such cases, the administration of another drug may be indicated, whether in place of or in addition to the originally delivered drug. Conventional osmotic pumps, however, are single drug or single drug combination devices: they can only infuse a single drug or a single combination of drugs at a time. To administer another drug, several alternatives are available, all of which involve significant discomfort to the patient. One such alternative is to administer the other drug intravenously while the osmotic pump remains implanted. Another alternative is to surgically remove the originally implanted drug and to implant another osmotic pump configured to deliver the other drug. These alternatives are also the only ones available when the implanted osmotic pump fails to function or runs out of drug, whether at the end of its useful life or whether the pump fails unexpectedly. What are also needed, therefore, are implantable osmotic pump systems configured for the selective delivery of more than one drug or more than one drug combination, at individually selectable rates. Also needed are implantable osmotic pump systems that include a built-in backup drug delivery system, the backup system being effective to continue the delivery of the drug when the primary delivery system reaches the end of its useful life or fails unexpectedly.

SUMMARY OF THE INVENTION

It is an object of the present invention, therefore, to provide novel implantable pumps and pump systems adapted to deliver a drug at more than a single rate. It is another object of the present invention to provide implantable osmotic pump systems configured for the selective delivery of more than one drug or more than one drug combination, at individually selectable rates. A still further object of the present invention is to provide osmotic pump systems that include a built-in backup drug delivery system, the backup system being effective to continue the delivery of the drug when the primary delivery system reaches the end of its useful life or fails unexpectedly.

In accordance with the above-described objects and those that will be mentioned and will become apparent below, an implantable osmotic pump system, according to an embodiment of the present invention includes a first osmotic pump including a first semipermeable membrane; a second osmotic pump including a second semipermeable membrane, and a single catheter attached to both the first and the second osmotic pumps.

The catheter may include a first lumen and a second lumen, the first lumen being connected to the first osmotic pump and the second lumen being connected to the second pump. Alternatively, the catheter may include a single lumen with two side arms, one of the two side arms being attached to the first pump and the other of the two side arms being attached to the second pump, each of two side arms including an internal lumen that feeds into the single lumen. The second semipermeable membrane may be sealed by an impermeable membrane. The impermeable membrane may be disposed over and away from semipermeable membrane so as to define a fluid tight compartment therewith. The impermeable membrane may be adapted to be punctured with a lancet when the pump system is implanted in a patient and may include, for example, titanium, stainless steel, a polymer such as polyethylene, polyethylene terephthalate (PET) or PETG and/or any biologically inert material adapted to be breached by a lancet or like device.

The first and second pumps may be preloaded with one or more pharmaceutical agents. The first pump may be preloaded with a first pharmaceutical agent at a first therapeutically effective concentration and the second pump may be preloaded with a second pharmaceutical agent at a second therapeutically effective concentration. The first pharmaceutical agent may be the same pharmaceutical agent as the second pharmaceutical agent or a different agent. Likewise, the first concentration may be at the same or different as the second concentration. The first pharmaceutical agent may potentiate a therapeutic property of the second pharmaceutical agent. For example, the first pharmaceutical agent may be an opioid and the second pharmaceutical agent may include a drug that potentiates an analgesic property of the first pharmaceutical agent, such as the alpha 2-adrenoreceptor agonist Clonidine.

The first pump may be preloaded with a first opioid and the first pump may be adapted to infuse the first opioid at a first therapeutically effective range of concentration. Likewise, the second pump may be preloaded with a second opioid and the second pump may be adapted to infuse the second opioid at a second therapeutically effective range of concentration after the semipermeable membrane is breached. The first opioid may include Fentanyl and/or Sufentanil and the second opioid may include Fentanyl and/or Sufentanil. The first opioid may be the same opioid as the second opioid and the second pump may be adapted to infuse the second opioid at the first therapeutically effective range when the first pump is out of the first opioid, upon breaching the impermeable membrane.

The present invention may also be viewed as a kit, comprising a first osmotic pump including a first semipermeable membrane; a second osmotic pump including a second semipermeable membrane, and a single catheter adapted to attach to both the first and the second osmotic pumps.

The second semipermeable membrane may be sealed by an impermeable membrane. The impermeable membrane may be disposed over and away from the one of the first and second semipermeable membrane so as to define a fluid tight compartment therewith. A lancet configured to breach the impermeable membrane may also be included in the kit. The first and second osmotic pumps may be preloaded with first and second pharmaceutical agent(s), respectively. For example, the first pharmaceutical agent may include Fentanyl and the second pharmaceutical agent includes Sufentanil. Alternatively, the first pharmaceutical agent may include Sufentanil and the second pharmaceutical agent may include Clonidine.

The present invention is also a drug delivery method, comprising the steps of infusing a first drug at a first therapeutically effective range of concentration from a first implanted osmotic pump; infusing a second drug at a second therapeutically effective range of concentration from a second implanted osmotic pump; preventing the first and second drugs from mixing until both the first and second drugs reach an intended delivery site.

The preventing step may be carried out by attaching a catheter having a first and a second lumen to the first and second osmotic pumps, the first lumen being in fluid communication with the first osmotic pump and the second lumen being in fluid communication with the second osmotic pump, a free end of the catheter being disposed at the intended delivery site. The first and second drugs may be therapeutically effective for pain therapy, hormone therapy, gene therapy, angiogenic therapy, anti-tumor therapy, chemotherapy and/or other pharmaceutical therapies.

According to another aspect thereof, the present invention is an implantable osmotic pump system, comprising: a first osmotic pump, including a first semipermeable membrane; a first impermeable membrane initially sealing the first semipermeable membrane; a second semipermeable membrane and a second impermeable membrane initially sealing the second semipermeable membrane, and a second osmotic pump, including a third semipermeable membrane; a third impermeable membrane initially sealing the third semipermeable membrane; a fourth semipermeable membrane and a fourth impermeable membrane initially sealing the fourth semipermeable membrane.

Each of the first and second pumps may include a proximal end, a distal end and a sidewall. One or both of the first and second initially sealed semipermeable membranes may be fitted to a side wall of the first pump and one or both of the third and fourth initially sealed semipermeable membranes may be fitted to a side wall of the second pump. Each of the first and second pumps may include a proximal and a distal end, and a catheter may be attached to the distal end of the first pump and to the distal end of the second pump. Each of the first to fourth impermeable membranes may be disposed over and away from the first to fourth semipermeable membranes, respectively, so as to define a first to fourth fluid tight compartment therewith, respectively. Each of the first to fourth impermeable membranes may be adapted to be punctured with a lancet when the pump system is implanted in a patient. The impermeable membranes may include titanium, stainless steel, platinum-iridium, polyethylene, PET and PETG and/or any biologically inert material that is impermeable to water. The first and second pumps may be preloaded with pharmaceutical agent(s). For example, the first pump may be adapted to deliver a dose of Fentanyl of about 10 to about 300 milligrams per day and the second pump may be adapted to deliver a dose of Sufentanil of about 1 to about 25 micrograms per day. Alternately, the first pump may be adapted to deliver a dose of Sufentanil of about 1 to about 25 micrograms per day and the second pump may be adapted to deliver a dose of Clonidine of about 25 to about 150 micrograms per day.

This pump system may be used by carrying out steps of breaching the first impermeable membrane; implanting the pump system into a patient to start infusion of the first pharmaceutical agent at a first therapeutically effective dose; breaching the second impermeable membrane to start infusion of the first pharmaceutical agent at a second therapeutically effective dose when the patient develops a tolerance to the first dose; breaching the third impermeable membrane to start infusion of the second pharmaceutical agent at a third therapeutically effective dose when the patient develops a tolerance to the first pharmaceutical agent, and breaching the fourth impermeable membrane to start infusion of the second pharmaceutical agent at a fourth therapeutically effective dose when the patient develops a tolerance to the third dose. The breaching steps may be carried out by puncturing the first to fourth impermeable membranes with a lancet.

According to still another embodiment, an implantable osmotic pump, comprises a pump housing having a proximal end, a distal end and a sidewall, the pump housing defining a pharmaceutical agent compartment and an osmotic agent compartment, the pharmaceutical agent compartment being separated from the osmotic agent compartment by a movable piston; a first semipermeable membrane fitted to the proximal end and a second semipermeable membrane fitted to a portion of the sidewall defining the osmotic engine compartment, both the first and second semipermeable membranes being adapted to allow water to cross into the osmotic engine compartment; an impermeable membrane sealing the second semipermeable membrane, and an integrated lancet adapted to breach the impermeable membrane.

The integrated lancet mechanism may be adapted to breach the impermeable membrane upon a manual application of force on the mechanism. A spring may bias a lancet away from the impermeable membrane. The integrated lancet mechanism may include a plurality of through holes, the through holes allowing water into the mechanism and in contact with the second semipermeable membrane when the impermeable membrane is breached. The pharmaceutical agent compartment may be preloaded with a pharmaceutical agent and the pump may be configured to infuse the pharmaceutical agent at a first rate based upon a composition, thickness and surface area of the first semipermeable membrane when the impermeable membrane is intact and may be configured to infuse the pharmaceutical agent at a second infusion rate when the impermeable membrane has been breached. The second rate may be based upon the composition, thickness and surface area of the first and the second semipermeable membranes. The pharmaceutical agent may include Fentanyl, infused within the range of about 10 to about 300 milligrams per day. The pharmaceutical agent may include a combination of Fentanyl and Sufentanil, infused within the range of about 1 to about 25 micrograms per day for Sufentanil and within the range of about 10 to about 30 milligrams per day of Fentanyl. Alternately still, the pharmaceutical agent may include a combination of Sufentanil and Clonidine, infused within a range of about 1 to about 25 micrograms per day for Sufentanil and within a range of about 25 to about 150 micrograms per day for Clonidine.

A method of delivering a pharmaceutical agent, according to a still further embodiment, comprises the steps of implanting an osmotic pump including a first and a second semipermeable membrane, the second impermeable membrane being initially sealed by an impermeable membrane, the pump including an integrated lancet mechanism adapted to breach the impermeable membrane; infusing the pharmaceutical agent at a first infusion rate based upon a composition, thickness and surface area of the first semipermeable membrane; applying force to the lancet mechanism to cause the mechanism to breach the impermeable membrane and expose the initially sealed second semipermeable membrane, and infusing the pharmaceutical agent at a second infusion rate that is higher than the first infusion rate, the second infusion rate being based upon a composition, thickness and surface area of the first and the second semipermeable membranes. The force-applying step may be carried out while the pump is implanted. A further step of palpating the implanted pump to locate the integrated lancet mechanism thereof prior to the force-applying step may also be carried out.

An implantable osmotic pump system, according to another embodiment of the present invention, comprises a pump housing having a proximal end, a distal end and a sidewall, the pump housing defining a pharmaceutical agent compartment and an osmotic agent compartment, the pharmaceutical agent compartment being separated from the osmotic agent compartment by a movable piston; a first semipermeable membrane fitted to a portion of the sidewall defining the osmotic engine compartment, the first semipermeable membrane being adapted to allow water to cross into the osmotic engine compartment and a first sealing member covering and sealing the first semipermeable membrane.

The proximal end of the pump housing may be impermeable to water. The first sealing is member may include a spacer fitted to the sidewall, the spacer including an impermeable membrane that is adapted to be breached by a lancet. The pump housing and the spacer may be configured to allow the spacer to be screwed on the sidewall. The spacer may be fitted to the pump housing by an ultrasonic weld.

The system may further include at least one second semipermeable membrane fitted to the portion of the sidewall defining the osmotic engine compartment, the second semipermeable membrane(s) being adapted to allow water to cross into the osmotic engine compartment; at least one second sealing member covering and sealing a respective one of the at least one second semipermeable membrane. The first and the at least one second sealing members may each include a spacer fitted to the sidewall, the spacer including an impermeable membrane that is adapted to be breached by a lancet. The impermeable membrane may be visible under fluoroscopy. At least the portion of the sidewall defining the osmotic engine compartment may be substantially flat and the pump housing may have a generally rectangular shape with rounded atraumatic edges.

BRIEF DESCRIPTION OF THE DRAWINGS

For a further understanding of the objects and advantages of the present invention, reference should be made to the following detailed description, taken in conjunction with the accompanying figures, in which:

FIG. 1a illustrates an implantable osmotic pump system including a first and second implantable pump connected to a dual lumen catheter, the pump system being in a state wherein the second pump is not enabled.

FIG. 1b illustrates the implantable pump system of FIG. 1a, in a state wherein the second pump is being enabled.

FIG. 1c illustrates an implantable osmotic pump system according to a further embodiment of the present invention, wherein the pump system is in a state wherein the second pump is fully enabled and wherein the pump system is connected to a single lumen catheter.

FIG. 4a shows a top view of an implantable osmotic pump system, according to a still further embodiment of the present invention.

FIG. 4b shows a side view of the implantable osmotic pump system of FIG. 4a.

FIG. 5 shows a top view of an intact impermeable membrane suitable for use with the pump systems of FIGS. 1a through 4b, as seen through fluoroscopy.

FIG. 6 shows a top view of the impermeable membrane of FIG. 5, after having been breached by a lancet, as seen through fluoroscopy.

DESCRIPTION OF THE INVENTION

Figure 2A:
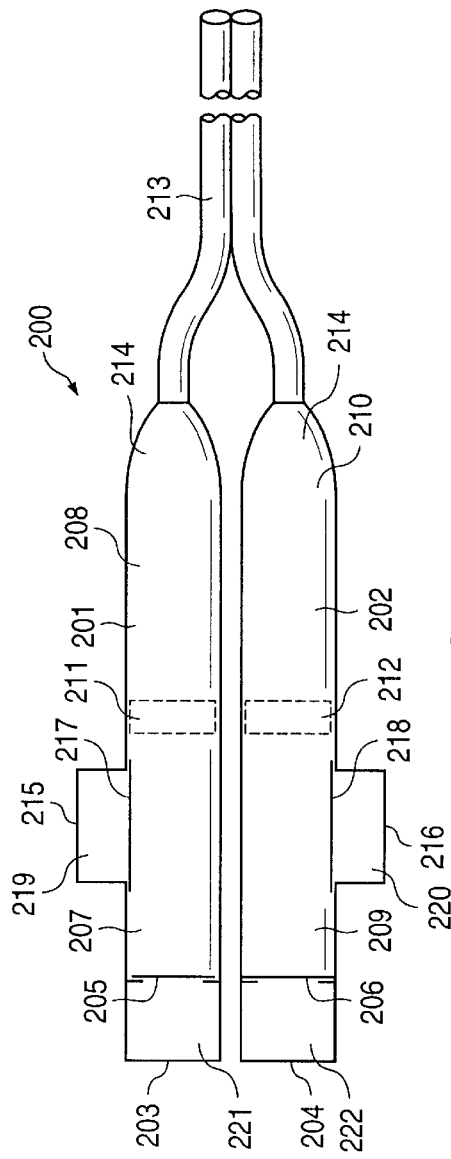
FIG. 2a illustrates an implantable osmotic pump system according to another embodiment of the present invention, wherein the pump system is connected to a dual lumen catheter.

FIG. 1a illustrates an implantable osmotic delivery system, kit and method according to an embodiment of the present invention. As shown therein, the osmotic pump system 100 according to the present invention includes a first pump 101 and a second pump 102. The first and pump 101 includes an osmotic engine compartment 107 and a pharmaceutical agent compartment 108 that are separated from one another by a movable piston 111 (shown in dashed lines). Similarly, the second implantable osmotic pump 102 includes an osmotic engine compartment 109 and a pharmaceutical agent compartment 110 that are separated from one another by a movable piston 112 (also shown in dashed lines). Each of the osmotic pumps 101 and 102 has a proximal and a distal end. A catheter 113 is attached to the distal end of each of the first and second pumps 101, 102. The catheter 113 may be a dual lumen catheter as shown in FIGS. 1a and 1b and include a first lumen and a second lumen, the first lumen being connected to the first osmotic pump 101 and the second lumen being connected to the second pump 102. One advantage of a dual lumen catheter, such as shown at reference numeral 113 in FIGS. 1a and 1b is that pharmaceutical agents (infused from the first and second pumps 101, 102) that interact can be infused and intentionally not mixed together until they reach the intended delivery site. This may be useful for such drug delivery applications such as hormone therapy or chemotherapy.

Alternatively, the catheter 113 may be a single lumen catheter as shown in FIG. 1c. Such a catheter 113 may include a single lumen with two side arms, one of the two side arms being attached to the first pump 101 and the other of the two side arms being attached to the second pump 102, each of two side arms including an internal lumen that feeds into the single lumen. In whichever configuration, an internal lumen of the catheter is in fluid communication with each of the pharmaceutical agent compartments 108, 110 of the first and second pumps 101, 102, respectively.

The proximal end of each of the first and second implantable osmotic pumps 101, 102 is fitted with a semipermeable membrane 104, 105 through which water from the patient may cross to reach the osmotic engine compartments 107, 109, respectively. Each of the semipermeable membranes 104, 105 may include, for example, a cellulose acetate composition. When the semipermeable membranes 104, 105 come into contact with water from the patient, the differential osmotic pressure across the semipermeable membranes 104, 105 causes the material in the osmotic engine compartments 107, 109 (i.e., the osmotic engine) to enlarge in volume and push on the movable piston 111, 112, respectively. This pushing of the movable pistons 111, 112 in the distal direction causes a corresponding decrease in the volume of the pharmaceutical agent compartments 108, 110 and causes the pharmaceutical agent(s) 114 contained therein to infuse through the infusion lumen(s) of the catheter 113 to the intended delivery site at the distal most end of the catheter 113.

As shown in FIGS. 1a through 1c, the semipermeable membrane 105 of the second pump 102 may be initially sealed by an impermeable membrane 103. Indeed, the impermeable membrane 103 may be disposed over and away from the semipermeable membrane 105 fitted to the proximal end of the second osmotic pump 102 so as to define a fluid tight compartment therewith. The impermeable membrane 103 may be adapted, according to an embodiment of the present invention, to be punctured with a lancet 115 when the pump system 100 is implanted in a patient (not shown). The impermeable membrane 103 may include titanium, stainless steel, platinum-iridium, polyethylene, PET and PETG, for example. Alternatively, the impermeable membrane 103 may be formed of any material or combinations of biologically inert materials that are impermeable to water and are adapted to be breached upon the application of force thereon with a lancet or like device.

According to an embodiment of the present invention, each of the first and second pumps 101, 102 may be preloaded with one or more pharmaceutical agents. That is, the pharmaceutical agent compartment 108 of the first pump 101 may be preloaded with one or more pharmaceutical agents 114 and the pharmaceutical agent compartment 110 of the second pump 102 may be preloaded with one or more pharmaceutical agents 114. The first pump 101 may be preloaded with a first pharmaceutical agent 114 at a first therapeutically effective concentration and the second pump 102 may be preloaded with a second pharmaceutical agent 114 at a second therapeutically effective concentration. The first pump 101 may be preloaded with the same or different than the pharmaceutical agent 114 preloaded in the second pump 102. Similarly, the concentration of the pharmaceutical agent 114 in the first pump 101 may be the same or different than the concentration of the pharmaceutical agent 114 in the second pump 102.

According to an advantageous embodiment of the present invention, the pharmaceutical agent 114 preloaded in one of the pumps 101, 102 potentiates the therapeutic property or properties of the pharmaceutical agent 114 preloaded in the other of the pumps 101, 102. For example, one of the pumps 101,102 may be preloaded with an opioid and the other of the pumps 101, 102 may be preloaded with a pharmaceutical agent that potentiates the analgesic property of the opioid. For example, the first pump 101 may be preloaded with Sufentanil and the second pump 102 may be preloaded with a drug or a combination of drugs that includes one or more alpha 2-adrenoreceptor agonists. An example of such an alpha 2-adrenoreceptor agonist is Clonidine, which is a drug that potentiates the analgesic properties of Sufentanil.

As shown in FIGS. 1a through 1c, the first pump 101 infuses the pharmaceutical agent 114 preloaded therein after the system 100 is implanted into the patient, as its semipermeable membrane 104 is in contact with water from the patient's body. The second pump 102, however, does not initially infuse any pharmaceutical agent 114 into the patient, as its semipermeable membrane 105 is initially sealed (FIG. 1a) from the patient by the impermeable membrane 103. A cylindrical spacer 106 may support the impermeable membrane 103 over the semipermeable membrane 105 so as to define a fluid tight compartment therewith. The fluid tight compartment may be filled with a saturated saline solution, to thereby maintain equal osmotic pressure on either side of the semipermeable membrane 105.

When the patient develops a tolerance to the pharmaceutical agent 114 infused by the first pump 101 or when the first pump 101 runs out of pharmaceutical agent 114 or otherwise unexpectedly fails, the surgeon may locate (by palpation or by an imaging technique such as fluoroscopy, for example) the impermeable membrane 103 and puncture it through the patient's skin. This may be done while the system 100 is fully implanted in the patient. When the impermeable membrane 103 is breached by a lancet 115 or the like, water (shown by the arrows leading toward the semipermeable membrane 105) from the patient may now reach the semipermeable membrane 105 and increase the osmotic differential pressure across the semipermeable membrane 105 and cause the second osmotic pump 102 to begin infusing the pharmaceutical agent(s) preloaded therein. When the second pump 102 is used as a backup, the second pump 102 significantly increases the useful life of the system 101. When used with the first pump 101, the second pump 102 allows the pump system 100 to deliver an increased dose of pharmaceutical agent 114 or a more therapeutically potent combination of drugs than would be possible with only a single pump.

Figure 2B:
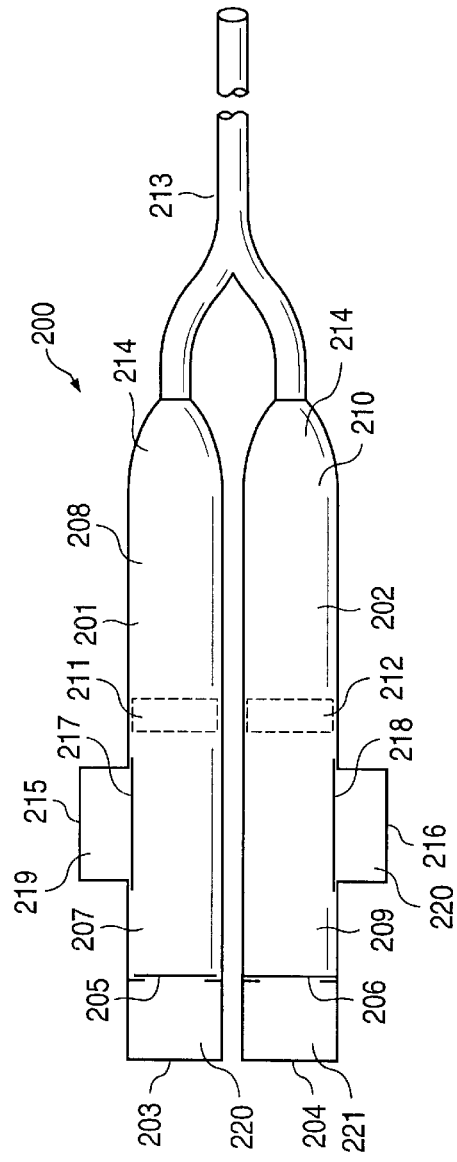
FIG. 2b illustrates an implantable osmotic pump system according to a still further embodiment of the present invention, wherein the pump system is connected to a single lumen catheter.

FIG. 2a illustrates an implantable osmotic pump system 200 according to another embodiment of the present invention. The pump system 200 of FIG. 2a is connected to a dual lumen catheter 213. FIG. 2b illustrates an implantable osmotic pump system 200 according to a further embodiment of the present invention, wherein the pump system 200 is connected to a single lumen catheter 213. Considering now FIGS. 2a and 2b collectively, the osmotic pump system 200 shown therein includes a first osmotic pump 201 and a second osmotic pump 202. The first osmotic pump 201 includes a first semipermeable membrane 205 and a first impermeable membrane 203 initially sealing the first semipermeable membrane 205. The first osmotic pump 201 also includes a second semipermeable membrane 217 and a second impermeable membrane 215 initially sealing the second semipermeable membrane 217. The second osmotic pump 202 includes a third semipermeable membrane 206 and a third impermeable membrane 204 initially sealing the third semipermeable membrane 206. The second pump 202 also includes a fourth semipermeable membrane 218 and a fourth impermeable membrane 216 initially sealing the fourth semipermeable membrane 218. The first implantable osmotic pump 201 and the second implantable osmotic pump 202 are each connected to two single (FIG. 2b) or to one dual (FIG. 2a) lumen catheter 213.

As shown in FIGS. 2a and 2b, at least one of the first and second semipermeable membranes 205, 217 of the first osmotic pump 201 is fitted to a sidewall of the first pump 201. FIGS. 2a and 2b show the first semipermeable membrane 205 fitted to the proximal end of the pump 201. However, both the first and the second semipermeable membranes 205, 217 may be fitted to the sidewall of the first pump 201, which may facilitate access thereto, depending on the orientation of the implanted pump system 200 within the patient. Likewise, at least one of the third and fourth semipermeable membranes 206, 218 of the second osmotic pump 202 is fitted to a sidewall of the second pump 202. FIGS. 2a and 2b show the third semipermeable membrane 206 fitted to the proximal end of the pump 202. However, both the third and fourth semipermeable membranes 206, 218 may be fitted to the sidewall of the second pump 202, as discussed above relative to the first pump 201. Alternatively still, the pump system 200 may be configured so as to fit any of the first to fourth semipermeable membranes 205, 217, 206, 218 to the respective proximal ends or sidewalls of the first and second pumps 201, 202, each of the first to fourth semipermeable membranes 205, 217, 206, 218 being initially sealed by the first to fourth impermeable membranes 20 203, 215, 204, 216, respectively. The impermeable membranes 203, 215, 204, 216 may, for example, be formed of or include titanium, stainless steel, platinum-iridium, polyethylene, PET and PETG or any other biologically inert material that is impermeable to water. According to an embodiment of the present invention, each of the first to fourth impermeable membranes 203, 215, 204, 216 may be disposed over and away from the first to fourth semipermeable membranes 205, 217, 206, 218, respectively, so as to define first to fourth fluid tight compartments 221, 219, 222, 220 therewith, respectively. Each of the first to fourth fluid tight compartments 221, 219, 222, 220 may include a volume of saturated saline solution therein, to maintain equal osmolarity across the semipermeable membranes 205, 217, 206, 218 until the impermeable membranes 203, 215, 204, 216 are breached (punctured, for example) by a lancet (115 in FIGS. 1a–1c) or other suitable device. According to the present invention, the second and fourth semipermeable membranes 217, 218 may be fitted to the sidewall of the first and second pumps 201, 202 in such a manner as to allow water to cross into the osmotic engine compartments 207, 209 of the first and second pumps 201, 202, respectively. In other words, the second and fourth semipermeable membrane 217, 218 are in fluid communication with the osmotic engine compartments 207, 209, respectively. As water crosses the first to fourth impermeable membranes 205, 217, 206, 218, the osmotic engine within each of the compartments 207, 209 expands and pushes upon respective movable pistons 211, 212 of the first and second pumps 201, 202 in the distal direction. This pushing correspondingly reduces the volumes of the therapeutic agent compartments 208, 210 and infuses the pharmaceutical agent(s) 214 from the first and second pumps 201, 202 and into the (single or dual lumen) catheter 213 to the delivery site within the patient.

According to the present invention, the system 200 may be implanted into the patient with at least one of the semipermeable membranes 205, 217, 206, 218 exposed. To do so, the surgeon would breach one of the first to fourth impermeable membranes 203, 215, 204, 216 immediately prior to implantation of the pump system 200 into the patient. The system 200 may also be implanted without any of the impermeable membranes 203, 215, 204, 216 breached. In that case, however, the pump system 200 will not begin infusing any pharmaceutical agent 214 until at least one of the impermeable membranes 203, 215, 204, 216 is breached to expose a corresponding semipermeable membrane 205, 217, 206, 218 to water from the patient.

Each of the first and second pumps 201, 202 may be preloaded with one or more pharmaceutical agents 214. Indeed, the first pump 201 may be preloaded with a first pharmaceutical agent 214 at a first therapeutically effective concentration. Likewise, the second pump 202 may be preloaded with a second pharmaceutical agent 214 at a second therapeutically effective concentration. The pumps 201, 202 may also infuse the pharmaceutical agent(s) 214 at a first and second therapeutically effective rate, wherein the first rate may be equal to or different to the second rate. The first pump 201 may be preloaded with a lesser or greater volume of the pharmaceutical agent 214 as may be preloaded into the second pump 202. The pumps 201, 202 may be preloaded with the same or a different pharmaceutical agent (opioids or non-opioids) 214 or combination(s) of pharmaceutical agents 214. In like manner, the concentrations of the pharmaceutical agent(s) 214 preloaded in the first and second pumps 201, 202 may be identical or dissimilar, depending upon the therapy prescribed by the patient's physician.

When the osmotic pump system 200 is used as a therapeutic tool within the context of pain management, for example, the system 200 may be implanted into the patient and the first impermeable membrane 203 may be breached by a lancet (as shown at 115 in FIGS. 1a, 1b and 1c) to start infusion of a first opioid (for example) at a first therapeutically effective dose. As the patient develops a tolerance to the first dose, or needs additional drug to relieve their pain, the second impermeable membrane 215 may be breached to start infusion of the first opioid at a second therapeutically effective dose. As the patient develops a tolerance to the first opioid, the third impermeable membrane 204 may be breached to start infusion of a second drug (opioid or non-opioid) at a third therapeutically effective dose. As the patient develops a tolerance to the third dose of the second drug or needs additional drug to relieve their pain, the fourth impermeable membrane 216 may be breached to start infusion of the second drug at a fourth therapeutically effective dose. It should be noted, however, that the sequence with which the impermeable membranes are breached may be modified at will. For example, the above-detailed sequence may be modified by substituting the second impermeable membrane 215 for the first impermeable membrane 203 and by substituting the fourth impermeable membrane 216 for the third impermeable membrane 204. Other sequences are possible. The first dose is dependent upon the surface area, thickness and composition of the first semipermeable membrane 205, as well as upon the degree of hydration of the implantation site within the patient. The second dose (which is infused when both the first and second semipermeable membranes 205, 217 are exposed to the patient) is dependent upon the first dose, as well as upon the surface are, thickness and composition of the second semipermeable membrane 217, as well as upon the degree of hydration of the implantation site within the patient. Similarly, the third dose is dependent upon the surface area, thickness and composition of the third semipermeable membrane 206, as well as upon the degree of hydration of the implantation site within the patient. The fourth dose (which is infused when both the third and fourth semipermeable membranes 206, 218 are exposed to the patient) is dependent upon the third dose, as well as upon the surface are, thickness and composition of the third semipermeable membrane 218, as well as upon the degree of hydration of the implantation site within the patient. These doses, therefore, may be selected by appropriately varying the above parameters upon manufacture of the pump system 200.

According to one advantageous embodiment, the first pharmaceutical agent 214 preloaded in the first osmotic pummel may potentiate a therapeutic property or properties of the second pharmaceutical agent 214 preloaded in the second osmotic pump 202, or vice-versa. For example, staying within the context of pain management, the first pharmaceutical agent 214 may be an opioid and the second pharmaceutical agent 214 may include a drug that potentiates an analgesic property or properties of the first pharmaceutical agent 214. For example, the first pharmaceutical agent may include Sufentanil and the second pharmaceutical agent 214 may include an alpha 2-adrenoreceptor agonist, such as Clonidine.

According to another embodiment of the present invention, the first and second osmotic pumps 201, 202 may be preloaded with first and second opioids, respectively. The first opioid may include Fentanyl and/or Sufentanil and the second opioid may also include Fentanyl and/or Sufentanil. For example, the first pump 201 may be adapted to deliver a dose of Fentanyl of about 10 to about 300 milligrams per day and the second pump 202 may be adapted to deliver a dose of Sufentanil of about 1 to about 25 micrograms per day, depending upon the clinical presentation of the patient. In the case wherein the first pump is preloaded with Sufentanil and the second pump is preloaded with an alpha 2-adrenoreceptor agonist such as Clonidine, the first pump 210 may be configured to deliver a dose of Sufentanil of about 1 to about 25 micrograms per day and the 115 second pump 202 may be adapted to deliver a dose of Clonidine of about 25 to about 150 micrograms per day, again depending upon the clinical presentation of the patient.

Figure 3A:
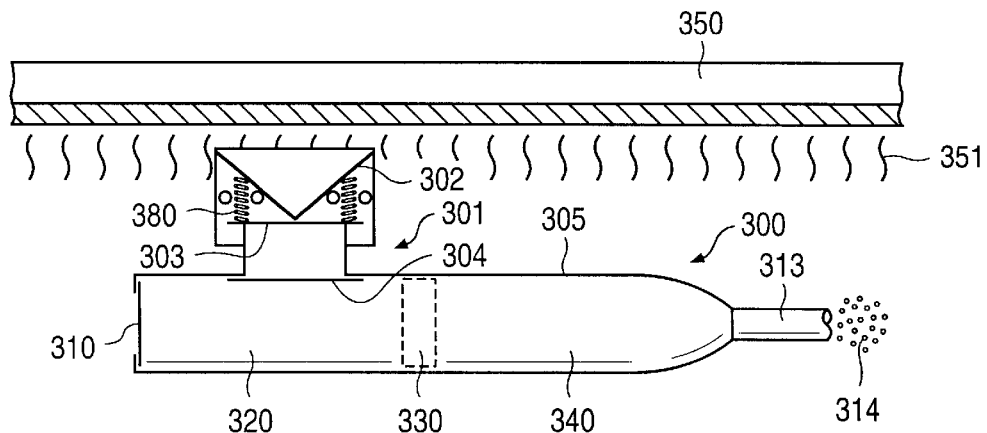
FIG. 3a illustrates an osmotic pump system and pharmaceutical agent delivery method, according to an embodiment of the present invention.
Figure 3B:
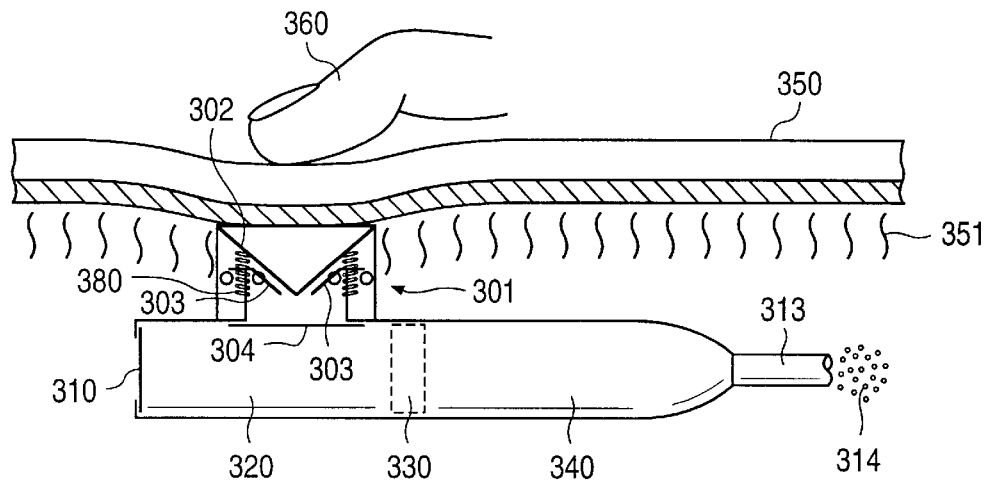
FIG. 3b illustrates the pump system of FIG. 3a, in a state wherein an impermeable membrane is being breached to expose a second semipermeable membrane to the patient environment.
Figure 3C:
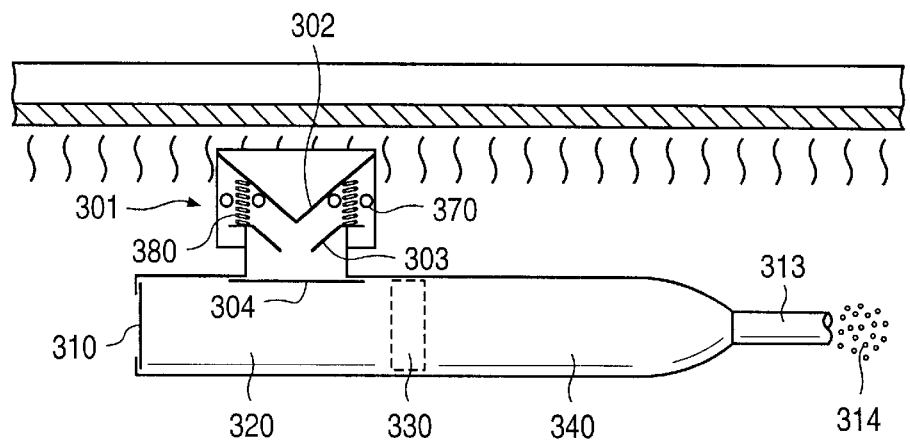
FIG. 3c illustrates the pump system of FIG. 3b, after the second semipermeable membrane has been exposed to the patient environment.

FIGS. 3a through 3c illustrate an osmotic pump system 300 and a pharmaceutical agent delivery method, according to a further embodiment of the present invention. As shown therein, the pump system 300 includes an integrated lancet mechanism 301 that may be actuated while the pump system 300 is implanted into the patient without, however, breaching the skin 350 and subcutaneous tissue 351 of the patient. Indeed, the implantable osmotic pump system 300 includes a catheter 313 and a pump housing 305 having a proximal end, a distal end and a sidewall, the pump housing 305 defining a pharmaceutical agent compartment 340 and an osmotic agent compartment 320. The pharmaceutical agent compartment 340 is separated from the osmotic agent compartment 320 by a movable piston 330 (shown in dashed lines in FIGS. 3a through 3c). A first semipermeable membrane 310 may be fitted to the proximal end of the pump system 300 and a second semipermeable membrane 304 may be fitted to a portion of the sidewall defining the osmotic engine compartment 320. Both the first and second semipermeable membranes 310, 304 allow water from the patient to cross into the osmotic engine compartment 320. As shown, an impermeable membrane 303 may seal the second semipermeable membrane 304. The integrated lancet mechanism 301 may be fitted over the impermeable membrane 303 such as to breach the underlying impermeable membrane 303 upon the application of force thereon. To bias the lancet mechanism 301 away from the impermeable membrane 303, the mechanism may include a spring 380, in compression. The spring 380 biases the lancet 302 of the mechanism 301 away from the impermeable membrane 303 for as long as the physician does not apply sufficient force on the mechanism to overcome the biasing force of the spring 380 and cause the lancet 302 to move in a direction normal to the longitudinal axis of the pump housing 305 to breach the impermeable membrane 304. This force on the mechanism 301 may be applied by means, for example, of the physician's thumb, shown at reference numeral 360 in FIG. 3b. Once breached, the impermeable membrane 303 allows water to reach the second semipermeable membrane 304 via the through holes 370 in the integrated lancet mechanism 301, as shown at FIG. 3c.

According to an embodiment of the present invention, the pharmaceutical agent compartment 340 may be preloaded with a pharmaceutical agent or agents 314 and the pump system 300 may be configured to infuse the pharmaceutical agent(s) at a first rate based upon the composition, thickness and surface area of the first semipermeable membrane 310 when the impermeable membrane 303 is intact. The pump system 300 may be configured to infuse the pharmaceutical agent(s) at a second infusion rate when the impermeable membrane 303 has been breached by the application of force to the integrated lancet mechanism 301. The second infusion rate, therefore, is based upon the composition, thickness and surface area of the second semipermeable membrane 304, as well as upon the first infusion rate. In other words, the second rate is the sum of the respective infusion rates contributed by each of the first and second semipermeable membranes 310, 304.

When the pump system 300 is first implanted in the patient, the first semipermeable membrane 310 is exposed to the osmotic pressure of the patient's subcutaneous tissue 351, which causes the osmotic engine within the osmotic engine compartment 320 to expand at a first rate based upon the surface area, composition and thickness of the first semipermeable membrane 310. In this state, the osmotic engine pushes against the movable piston 330, causing the pharmaceutical agent 314 to be infused at a first rate. When the patient develops a tolerance to the first infusion rate, the physician may locate the integrated lancet mechanism 301 (by feel or through an imaging technique) and apply force thereon with his or her finger 360, as shown in FIG. 3b. This causes the impermeable membrane 303 to be breached and the underlying second semipermeable membrane 304 to be exposed to the osmotic pressure of the patient's subcutaneous tissue 351. The osmotic engine is now expanding at a second rate that is related to the surface area, thickness and composition of the second semipermeable membrane 304, as well as that of the first semipermeable membrane 310. The osmotic engine then pushes on the movable piston 330, thereby causing the pharmaceutical agent to be infused at the second rate.

In one embodiment, a pharmaceutical agent 314 may be preloaded within the pharmaceutical agent compartment 340. For example, the compartment 340 may enclose Fentanyl, which may be infused within the range of about 10 to about 300 milligrams per day, dependent upon the clinical presentation of the patient and the delivery site. Alternatively, the pharmaceutical agent 314 may include a combination of Fentanyl and Sufentanil. Such a combination (mixture) may be infused at a rate selected within the range of about 1 to about 25 micrograms of Sufentanil per day, again depending upon the clinical presentation of the patient and the delivery site of the drug within the patient. Alternatively still, the pharmaceutical agent 314 may be or include a combination of Sufentanil and Clonidine, which combination may be infused within a range of about 1 to about 25 micrograms per day for Sufentanil and within a range of about 25 to about 150 micrograms per day for Clonidine, both dependent upon the clinical presentation of the patient and the delivery site.

Pain management medications are not the only medications for which the devices, methods and systems disclosed herein find advantageous application. Indeed, the pharmaceutical agent compartment 340 may be preloaded with one or more pharmaceutical agents that are therapeutically effective for hormone therapy, gene therapy, angiogenic therapy, anti-tumor therapy, chemotherapy and/or other therapies.

FIG. 4a shows a top view of an implantable osmotic pump system 400, according to a still further embodiment of the present invention, whereas FIG. 4b shows a side view thereof. Considered collectively, FIGS. 4a and 4b show an implantable osmotic pump system 400 comprising a pump housing 401 having a proximal end, a distal end and a sidewall, the pump housing 401 defining a pharmaceutical agent compartment 440 and an osmotic agent compartment 420. The pharmaceutical agent compartment 440 is separated from the osmotic agent compartment 420 by a movable piston 412, shown in dashed lines. A first semipermeable membrane 404 is fitted to a portion of the sidewall defining the osmotic engine compartment 420 and is adapted to allow water to cross into the osmotic engine compartment 420 because of the osmotic pressure at the implantation site. A first sealing member 406 covers and seals the first semipermeable membrane 404. A catheter 413 may be attached to the distal end of the pump housing 401, the catheter 413 being in fluid communication with the pharmaceutical agent compartment 440. As shown in FIGS. 4a and 4b, the proximal end of the pump housing 401 is impermeable to water, as it does not include a semipermeable membrane fitted thereto, unlike the device shown in FIGS. 1a through 3c.

The first sealing member 406 may include a (cylindrical, for example) spacer 415 fitted to the sidewall, the spacer 415 being covered by an impermeable membrane 407 that is adapted to be breached by a lancet. The pump housing 401 and the spacer 415 may each include mating threads to allow the spacer 415 to be screwed on the sidewall. Alternatively, the spacer 415 may be fitted to the pump housing 401 by an ultrasonic weld. The impermeable membrane 407 may include, for example, titanium, stainless steel, platinum-iridium, polyethylene, PET and PETG or any biologically inert material that is impermeable to water.

As shown most clearly in FIG. 4b, at least one second semipermeable membrane 405 may be fitted to the portion of the sidewall defining the osmotic engine compartment 420, the second semipermeable membrane(s) 405 being adapted to allow water to cross into the osmotic engine compartment 420 when subjected to osmotic pressure from the patient. Each of the second semipermeable membranes 405 may be covered and sealed by a respective second sealing member 406. In turn, the second sealing member(s) 406 include a spacer 415 fitted to the sidewall, the spacer 415 including an impermeable membrane 407 (FIG. 4b) that is adapted to be breached by a lancet, as shown at reference 115 in FIGS. 1a through 1c. To facilitate localization of the impermeable membrane(s) 407 after the system 400 is implanted into the patient, the impermeable membrane(s) 407 may include a radiopaque material—a material that is visible under fluoroscopy. For example, the impermeable membrane(s) 407 may include titanium, stainless steel, platinum, platinum-iridium, PET and/or PETG. To render the membrane(s) 407 made of PET or PETG visible under fluoroscopy, a radiopaque material such as gold or aluminum, for example, may be sputtered thereon. FIG. 5 shows a top view of an intact impermeable membrane 407, whereas FIG. 6 shows a top view of the same impermeable membrane 407 after being breached by a lancet.

As shown in FIG. 4a, the pump housing 401 may accommodate an array of semipermeable membranes 404, 405, each initially covered and sealed by a sealing member 406. Each semipermeable membrane 404, 405, in turn, may be exposed to the patient's osmotic pressure by breaching an impermeable membrane 407 covering each sealing member 406. To accommodate these semipermeable membranes 404, 405 and their corresponding sealing members 406, at least the portion of the sidewall defining the osmotic engine compartment 420 may be substantially flat, as most clearly shown in FIG. 4b. In turn, to accommodate this substantially flat sidewall portion, the pump housing 401 may have a generally rectangular shape with rounded, atraumatic edges. Each sealing member 406, as detailed with respect to FIGS. 3a through 3c, may be fitted with an integrated lancet mechanism 301 (FIGS. 3a–3c) adapted to breach the impermeable membrane 407 of the sealing member 406 to expose the underlying semipermeable membrane 404 or 405. As with the embodiments of FIGS. 1a through 3c, each of the sealing members 406 may define a fluid tight compartment with a respective underling semipermeable membrane 404, 405. These fluid tight compartments may be filled with a saturated saline solution to maintain equal osmolarity on either side of the semipermeable membrane 404, 405 until the semipermeable membrane 404, 405 is exposed to water from the patient, as disclosed in co-pending and commonly assigned U.S. patent application Ser. No. 09/442,128 filed on Nov. 6, 1999 and entitled "Methods And Implantable Devices And Systems For Long Term Delivery Of A Pharmaceutical Agent" and/or co-pending and commonly assigned U.S. patent application entitled "Osmotic Pump Delivery System With Pre-Hydrated Membrane And Primable Catheter", attorney docket number MICR5646, the disclosures of both of which are hereby incorporated herein in their entireties.

Upon implantation of the pump system 400, the first semipermeable membrane 404 is exposed to the osmotic pressure of the patient, which causes the osmotic engine within the osmotic engine compartment 420 to expand at a first rate based upon the surface area, composition and thickness of the first semipermeable membrane 404. In this state, the osmotic engine pushes against the movable piston 412, causing the pharmaceutical agent 414 to be infused at a first rate. When the patient develops a tolerance to the first infusion rate, the physician may locate one of the second sealing members 406 by touch or by fluoroscopy, for example, and breach the impermeable membrane 407 thereof (as shown by the dashed lines of the breached impermeable membrane 407 in FIG. 4b). This causes the corresponding underlying second semipermeable membrane 405 to be exposed to the osmotic pressure of the patient. The osmotic engine now expands at a second rate that is related to the surface area, thickness and composition of the second semipermeable membrane 405, as well as that of the first semipermeable membrane 404. The osmotic engine then pushes on the movable piston 412, thereby causing the pharmaceutical agent 414 to be infused at the second rate. As the patient develops a tolerance to the second rate, another sealing member 406 is located, the impermeable membrane 407 thereof breached to thereby cause the pharmaceutical agent 414 to be infused at a third rate. Additional impermeable members 407 are breached as the patient develops a tolerance to the previous infusion rate, until the desired therapeutic effect is achieved.

The pump system 400 may be preloaded with the same variety of drugs discussed above relative to FIGS. 3a through 3c and the description thereof is incorporated herein in its entirety, as if repeated here in full.

While the foregoing detailed description has described preferred embodiments of the present invention, it is to be understood that the above description is illustrative only and not limiting of the disclosed invention. Those of skill in this art will recognize other alternative embodiments and all such embodiments are deemed to fall within the scope of the present invention. Thus, the present invention should be limited only by the claims as set forth below.

What is claimed is:

1. An implantable osmotic pump system, comprising:
   a first osmotic pump including a first semipermeable membrane;
   a second osmotic pump including a second semipermeable membrane, and
   a single catheter attached to both the first and the second osmotic pumps.

2. The pump system of claim 1, wherein the catheter includes a first lumen and a second lumen, the first lumen being connected to the first osmotic pump and the second lumen being connected to the second pump.

3. The pump system of claim 1, wherein the catheter includes a single lumen with two side arms, one of the two side arms being attached to the first pump and the other of the two side arms being attached to the second pump, each of two side arms including an internal lumen that feeds into the single lumen.

4. The pump system of claim 1, wherein the second semipermeable membrane is sealed by an impermeable membrane.

5. The pump system of claim 4, wherein the impermeable membrane is disposed over and away from said one of the first and second semipermeable membranes so as to define a fluid tight compartment therewith, the fluid tight compartment being filled with a saturated saline solution.

6. The pump system of claim 4, wherein the impermeable membrane is adapted to be punctured with a lancet when the pump system is implanted in a patient.

7. The pump system of claim 4, wherein the impermeable membrane comprises at least one of titanium, stainless steel, platinum, platinum-iridium, polyethylene, PET and PETG.

8. The pump system of claim 4, wherein the first and second pumps are preloaded with at least one pharmaceutical agent.

9. The pump system of claim 4, wherein the first pump is preloaded with a first pharmaceutical agent at a first therapeutically effective concentration and wherein the second pump is preloaded with a second pharmaceutical agent at a second therapeutically effective concentration.

10. The pump system of claim 9, wherein the first pharmaceutical agent is a same pharmaceutical agent as the second pharmaceutical agent.

11. The pump system of claim 10, wherein the first concentration is a same concentration as the second concentration.

12. The pump system of claim 9, wherein the first pharmaceutical agent is a different pharmaceutical agent than the second pharmaceutical agent.

13. The pump system of claim 9, wherein the first pharmaceutical agent potentiates a therapeutic property of the second pharmaceutical agent.

14. The pump system of claim 9, wherein the first pharmaceutical agent is an opioid and wherein the second pharmaceutical agent includes a drug that potentiates an analgesic property of the first pharmaceutical agent.

15. The pump system of claim 14, wherein the first pharmaceutical agent includes Sufentanil and wherein the drug includes an alpha 2-adrenoreceptor agonist.

16. The pump system of claim 15, wherein the alpha 2-adrenoreceptor agonist includes Clonidine.

17. The pump system of claim 4, wherein the first pump is preloaded with a first opioid and wherein the first pump is adapted to infuse the first opioid at a first therapeutically effective range of concentration and wherein the second pump is preloaded with a second opioid and wherein the second pump is adapted to infuse the second opioid at a second therapeutically effective range of concentration after the semipermeable membrane is breached.

18. The pump system of claim 17, wherein the first opioid includes one of Fentanyl and Sufentanil and wherein the second opioid includes one of Fentanyl and Sufentanil.

19. The pump of claim 17, wherein the first opioid is a same opioid as the second opioid and wherein the second pump is adapted to infuse the second opioid at the first therapeutically effective range when the first pump is out of the first opioid, upon breaching the impermeable membrane.

20. The pump system of claim 1, wherein the first and second pumps are preloaded with at least one pharmaceutical agent.

21. The pump system of claim 1, wherein the first pump is preloaded with a first pharmaceutical agent at a first therapeutically effective concentration and wherein the second pump is preloaded with a second pharmaceutical agent at a second therapeutically effective concentration.

22. The pump system of claim 21, wherein the first pharmaceutical agent is a same pharmaceutical agent as the second pharmaceutical agent.

23. The pump system of claim 22, wherein the first concentration is a same concentration as the second concentration.

24. The pump system of claim 21, wherein the first pharmaceutical agent is a different pharmaceutical agent than the second pharmaceutical agent.

25. The pump system of claim 21, wherein the first pharmaceutical agent potentiates a therapeutic property of the second pharmaceutical agent.

26. The pump system of claim 21, wherein the first pharmaceutical agent is an opioid and wherein the second pharmaceutical agent includes a drug that potentiates an analgesic property of the first pharmaceutical agent.

27. The pump system of claim 26, wherein the first pharmaceutical agent includes Sufentanil and wherein the drug includes an alpha 2-adrenoreceptor agonist.

28. The pump system of claim 27, wherein the alpha 2-adrenoreceptor agonist includes at least one of Clonidine and derivatives of Clonidine.

29. A kit, comprising:
  a first osmotic pump including a first semipermeable membrane;
  a second osmotic pump including a second semipermeable membrane, and
  a single catheter adapted to attach to both the first and the second osmotic pumps.

30. The kit of claim 29, wherein the catheter includes a first lumen and a second lumen, the first lumen being adapted to connect to the first osmotic pump and the second lumen being adapted to connect to the second pump.

31. The kit of claim 29, wherein the catheter includes a single lumen with two side arms, one of the two side arms being adapted to attach to the first pump and the other of the two side arms being adapted to attach to the second pump, each of two side arms including an internal lumen that feeds into the single lumen.

32. The kit of claim 29, wherein the second semipermeable membrane is sealed by an impermeable membrane.

33. The kit of claim 32, wherein the impermeable membrane is disposed over and away from the said one of the first and second semipermeable membrane so as to define a fluid tight compartment therewith, the fluid tight compartment being filled with a saturated saline solution.

34. The kit of claim 32, further including a lancet configured to breach the impermeable membrane.

35. The kit of claim 29, wherein the first osmotic pumps is preloaded with a first pharmaceutical agent and wherein the second pump is preloaded with a second pharmaceutical agent.

36. The kit of claim 35, wherein the first pharmaceutical agent is a same pharmaceutical agent as the second pharmaceutical agent.

37. The kit of claim 35, wherein the first pharmaceutical agent is a different pharmaceutical agent as the second pharmaceutical agent.

38. A drug delivery method, comprising the steps of:
  infusing a first drug at a first therapeutically effective range of concentration from a first implanted osmotic pump;
  infusing a second drug at a second therapeutically effective range of concentration from a second implanted osmotic pump;
  preventing the first and second drugs from mixing until both the first and second drugs reach an intended delivery site by attaching a catheter having a first and a second lumen to the first and second osmotic pumps, the first lumen being in fluid communication with the first osmotic pump and the second lumen being in fluid communication with the second osmotic pump, a free end of the catheter being disposed at the intended delivery site.

39. The method of claim 38, wherein the first and second drugs are therapeutically effective for at least one therapy selected from pain therapy, hormone therapy, gene therapy, angiogenic therapy, anti-tumor therapy and chemotherapy.

* * * * *

UNITED STATES PATENT AND TRADEMARK OFFICE
CERTIFICATE OF CORRECTION

PATENT NO.    : 6,471,688 B1
DATED         : October 29, 2002
INVENTOR(S)   : Harper et al.

It is certified that error appears in the above-identified patent and that said Letters Patent is hereby corrected as shown below:

Column 17,
Line 1, should read as follows:
8. The pump system of claim 1, wherein the first and
Line 4, should read as follows:
9. The pump system of claim 1, wherein the first pump is Signed and Sealed this Fifteenth Day of April, 2003

JAMES E. ROGAN
*Director of the United States Patent and Trademark Office*